United States Patent [19]

Naito et al.

[11] Patent Number: 4,763,514
[45] Date of Patent: Aug. 16, 1988

[54] MONITORING EQUIPMENT FOR DISSOLVED GAS IN INSULATING OIL

[75] Inventors: Sadao Naito; Katsumi Shiono; Hideo Shinohara; Yoshihiro Makino; Toshitsugu Ishii, all of Ako, Japan

[73] Assignee: Mitsubishi Denki Kabushiki Kaisha, Japan

[21] Appl. No.: 862,967

[22] Filed: May 14, 1986

[51] Int. Cl.$^4$ ............................................... G01N 1/00
[52] U.S. Cl. ......................................... 73/19; 73/61 R
[58] Field of Search ................... 73/61 R, 61.1 R, 19, 73/863.21, 64; 55/55

[56] References Cited

U.S. PATENT DOCUMENTS

| | | | |
|---|---|---|---|
| 3,844,160 | 10/1974 | Yamaoka | 73/19 |
| 3,942,356 | 3/1976 | Branscombe et al. | 73/19 |
| 4,236,404 | 12/1980 | Ketchum et al. | 73/19 |
| 4,402,211 | 9/1983 | Sugawara et al. | 73/19 |
| 4,444,040 | 4/1984 | Sakai et al. | 73/19 |
| 4,510,060 | 4/1985 | Stewart et al. | 73/61 R |

FOREIGN PATENT DOCUMENTS

| | | | |
|---|---|---|---|
| 249033 | 12/1985 | Japan | 73/33 |
| 913152 | 3/1982 | U.S.S.R. | 73/19 |

OTHER PUBLICATIONS

"American National Standard Guide for the Detection and Determination of Generated Gases in Oil-Immersed Transformers and Their Relation to the Serviceability of the Equipment", ANSI/IEEE C57, 104–1978.
"Operating Manual for Incipient Fault Detector", Revision 1–80, Westinghouse Electric Corporation, 1980.

Primary Examiner—Stewart J. Levy
Assistant Examiner—Hezron E. Williams
Attorney, Agent, or Firm—Leydig, Voit & Mayer

[57] ABSTRACT

An apparatus for monitoring gas dissolved in an electrically insulating oil used in an electrical apparatus comprises a sampling device connected to a tank for sampling a portion of the insulating oil from the electrical apparatus, an extracting device connected to the sampling device for extracting a volume of dissolved gas from the portion of the insulating oil in the sampling device, and a measuring device connected to the extracting device for measuring the components of the dissolved gas. All of the volume of dissolved gas is delivered from the extracting device either by pumping the oil from the tank to the extracting device to force the dissolved gas to the measuring device or by using a plate of the extracting device to force the dissolved gas therefrom. All of the volume of dissolved gas measured is exhausted from the measuring device. The portion of the insulating oil remaining in the extracting device is returned to the tank.

18 Claims, 5 Drawing Sheets

MONITORING EQUIPMENT FOR DISSOLVED GAS IN INSULATING OIL

The present invention relates to an apparatus for monitoring dissolved gas in insulating oil contained in a tank in which an electrical device is immersed.

A conventional dissolved gas monitor, such as the one disclosed in Japanese Patent Publication No. 58-58802, is disposed to monitor and detect at an early stage combustible dissolved gases generated by abnormal phenomena such as arc discharge, corona discharge or localized heating within an electrical apparatus immersed in a tank. In such a monitor, an insulating oil circulating passage is connected to the tank at both ends thereof, and a gas detecting chamber for detecting the dissolved gas in the insulating oil is disposed in the insulating oil circulating passage. A space is formed within the upper portion of the gas detecting chamber through pressure reduction by adjusting a throttle valve, a pump for circulating the insulating oil, etc. disposed in the insulating oil circulating passage. The components of the dissolved gas collected within the upper space of the gas detecting chamber are measured by a gas detecting element disposed in the gas detecting chamber. The dissolved gas in the upper space may be transmitted to the tank through the insulating oil circulating passage, thereby adversely affecting the oil-immersed electrical apparatus within the tank.

Furthermore, in the monitor mentioned above, the insulating oil circulating passage is communicated with two oil ports of the tank on the side thereof. However, when a tank is provided with only a single oil port, the monitor cannot be easily connected to the tank.

Furthermore, conventional monitors are not provided with a device for removing foreign matter in the insulating oil flowing through the insulating oil circulating passage.

SUMMARY OF THE INVENTION

To overcome the problems mentioned above, an object of the present invention is to provide an apparatus for monitoring dissolved gas in an insulating oil in which the dissolved gas from the insulating oil transmitted from a tank of such oil in which an electrical apparatus is immersed is not transmitted back to the tank after its components are measured so that the oil-immersed electrical apparatus within the tank is not adversely reaffected by that dissolved gas.

Another object of the present invention is to provide an apparatus for monitoring dissolved gas in an insulating oil in which foreign matter in the circulated insulating oil are filtered.

Another object of the present invention is to provide an apparatus for monitoring dissolved gas in an insulating oil in which the monitor can be easily connected to a tank provided with an only single port for the insulating oil.

With the above objects in view, the present invention resides in a monitor for gas dissolved in an electrically insulating oil used in an electrical apparatus comprising sampling means connectable to the tank for sampling a portion of the insulating oil from the electrical apparatus, extracting means connected to said sampling means for extracting the dissolved gas from said portion of the insulating oil in said sampling means, measuring means connected to said extracting means for measuring the components of the dissolved gas from said extracting means, means for exhausting the dissolved gas measured in said measuring means, and means for returning said portion of the insulating oil in said extracting means to the electrical apparatus.

BRIEF DESCRIPTION OF THE DRAWINGS

The present invention will now be described with reference to the preferred embodiments thereof in conjunction with the drawings in which.

DETAILED DESCRIPTION OF THE PREFERRED EMBODIMENTS

Figure 1:
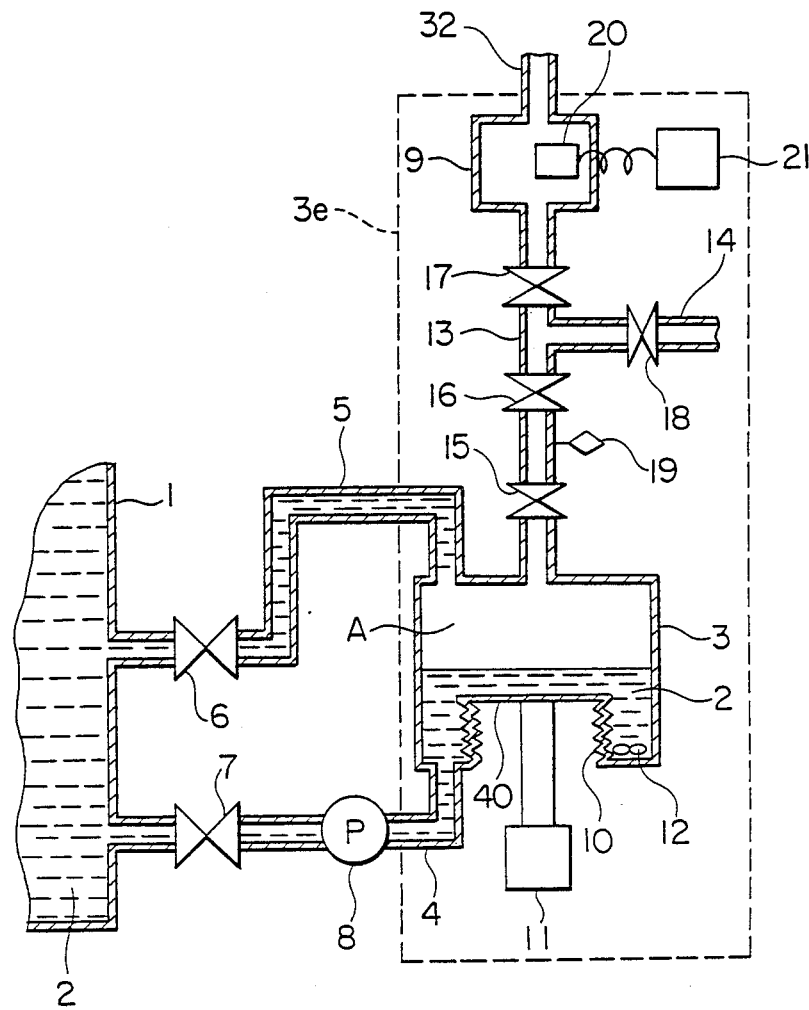
FIGS. 1 through 5 are respectively sectional views showing the first through fifth embodiments of an apparatus for monitoring dissolved gas in an insulating oil according to the present invention.

In FIG. 1, an electrical apparatus to which a monitor of the present invention can be applied comprises a tank 1 filled with an insulating oil 2 for electrically insulating an electrical device (not shown) in the tank 1. In the vicinity of the tank 1, there are disposed a gas extracting chamber 3 for sampling a portion of the insulating oil 2 from the tank 1 and extracting a dissolved gas from the sampled insulating oil, and a gas detecting chamber 9 for measuring the components of the dissolved gas which is in communication with the gas extracting chamber 3. According to the present invention, the gas measuring chamber 9 is opened to the atmosphere so that the measured gas may be exhausted to the atmosphere through a pipe 32. An insulating oil circulating passage for circulating the insulating oil 2 comprises an oil send-in conduit 4 and an oil send-out conduit 5 connected between the tank 1 and the gas extracting chamber 3. Valves 6 and 7 are respectively disposed in the oil send-out and send-in conduits 5 and 4, and are opened or closed to pass or interrupt the flow of the insulating oil therethrough. The oil send-in conduit 4 and the oil send-out conduit 5 are respectively connected to the lowermost and uppermost portions of the gas extracting chamber 3. A pump 8 for circulating the insulating oil 2 in the circulating passage is disposed in the oil send-in conduit 4 between the valve 7 and the gas extracting chamber 3. The oil send-in conduit 4, the oil send-out conduit 5 and the pump 8 as well as the gas extracting chamber 3 constitute an insulating oil circulating means. The insulating oil 2 in the circulating passage is circulated through the conduits 4 and 5 by the pump 8 between the tank 1 and the gas extracting chamber 3, until the insulating oil 2 within the gas extracting chamber 3 becomes a good sample of the body of the insulating oil within the tank 1.

An extracting means for extracting a dissolved gas from the insulating oil within the gas extracting chamber 3 comprises a plate 40, a bellows 10 attached to the plate 40 and a driving device 11 for reciprocating the plate 40 disposed in the lower portion of the gas extracting chamber 3. The bellows 10 and the plate 40 define the gas extracting chamber 3 and are moved to change the volume of the gas extracting chamber 3. When the driving device 11 is driven to move the plate 40 downwards in FIG. 1, a gas dissolved in the insulating oil within the gas extracting chamber 3 is extracted from the insulating oil amd forms a space of the dissolved gas under pressure reduction in the upper portion of the gas extracting chamber 3. A vibrator 12 may preferably be disposed within the gas extracting chamber 3 to forcibly extract the dissolved gas from the insulating oil 2 by vibrating the insulating oil.

The upper portion of the gas extracting chamber 3 is connected to a gas detecting chamber 9 through a gas conduit 13. An air conduit 14 is connected to the gas conduit 13 to introduce outside air into the gas extracting chamber 3. The oxygen in the outside air is used to detect the components of the dissolved gas in the gas detecting chamber 9, as described later. Valves 15, 16, 17 and 18 are respectively attached to the gas conduit 13 and the air conduit 14. The air conduit 14 is connected to a portion of the gas conduit 13 between the valves 16 and 17. A detector 19 for detecting the level of the insulating oil flowing through the gas conduit 13 is disposed between the valves 15 and 16. The valves 6, 15, 16 and 17 are set to be closed when the oil in the gas conduit 13 reaches oil level detector 19.

The dissolved gas within the gas extracting chamber 3 is flowed into the gas detecting chamber 9 through the gas conduit 13 as described later. The components of the dissolved gas within the gas detecting chamber 9 are measured by a gas detector for detecting combustible gas using oxygen in the air. The gas detector comprises a detecting element 20 disposed in the gas detecting chamber 9 and a gas detector main body 21 electrically connected to the detecting element 20. When a gas detector for detecting the components of the dissolved gas without using oxygen in the air is used, it is not necessary to introduce outside air into the gas extracting chamber so that there is no need to dispose the air conduit 14 and the valve 18 attached thereto. The gas detecting chamber 9 and the gas detector constitute a gas detecting means in communication with the gas extracting chamber 3 and measuring the components of the dissolved gas from the gas extracting chamber 3.

When the monitor mentioned above is operated, the valves 15, 16 and 18 are opened and the plate 40 is moved upwards to a predetermined position by the driving device 11. The insulating oil 2 from the tank 1 then fills the gas extracting chamber 3, the send-out conduit 5 and the send-in conduit 4. Then, the valves 15, 16 and 18 are closed and the insulating oil 2 is circulated by the pump 8 between the tank 1 and the gas extracting chamber 3 such that the insulating oil 2 within the gas extracting chamber 3 is typical of the insulating oil 2 within the tank 1. Thereafter, the operation of the pump 8 is stopped and the valves 6 and 7 are closed. The driving device 11 is then driven to move the plate 40 downwards so that dissolved gas is extracted from the insulating oil 2 within the gas extracting chamber 3 and forms a space A of the dissolved gas under pressure reduction in the upper portion of the gas extracting chamber 3. Preferably, the vibrator 12 is then vibrated to forcibly extract any remaining dissolved gas from the insulating oil to balance the density of the dissolved gas in the space A under pressure reduction with the density of the gas dissolved in the insulating oil within the gas extracting chamber 3. Then, the operation of the vibrator 12 is stopped and the valves 15, 16 and 18 are opened to introduce outside air into the space A through the air conduit 14 and the gas conduit 13. Then, the valve 18 is closed and the valve 6 is opened to flow the insulating oil 2 from the tank 1 into the gas extracting chamber 3. Simultaneously, the valve 17 is opened so that the mixture of the dissolved gas and the air within the space A is transmitted into the gas detecting chamber 9. The components of the dissolved gas in the mixed gas are measured by the gas detector having the gas detecting element 20 and the detector body 21. When the level of the insulating oil in the gas conduit 13 reaches the oil level detector 19, the valves 15, 16, 17 and 6 are closed, thereby completing the measurement of the components of the dissolved gas.

The mixture of the dissolved gas and the air in the gas extracting chamber 3 may also be transmitted to the gas detecting chamber 9 by moving the plate 40 upwards using the driving device 11 instead of by transmitting the insulating oil 2 in the tank 1 into the gas extracting chamber 3 as mentioned above.

In the first embodiment, the plate 40, the bellows 10 and the driving device 11 are used as a means for extracting the dissolved gas from the insulating oil within the gas extracting chamber 3. However, the dissolved gas can be extracted from the insulating oil even when the gas extracting chamber 3 is in the shape of a cylinder and the bottom of the gas extracting chamber 3 is defined by a piston or the like driven by a driving device.

According to the first embodiment of the present invention, insulating oil is transmitted from a tank in which an electrical apparatus is immersed in the insulating oil to a gas extracting chamber in which a device for extracting a dissolved gas from the insulating oil is disposed. According to the present invention, the dissolved gas in the gas extracting chamber flows to a gas detecting chamber which is open to the atmosphere. Therefore after the measurement, the dissolved gas is exhausted and not returned to the tank, so that the dissolved gas is not transmitted into the tank and therefore the electrical apparatus in the tank is not adversely affected by the dissolved gas.

Figure 2:
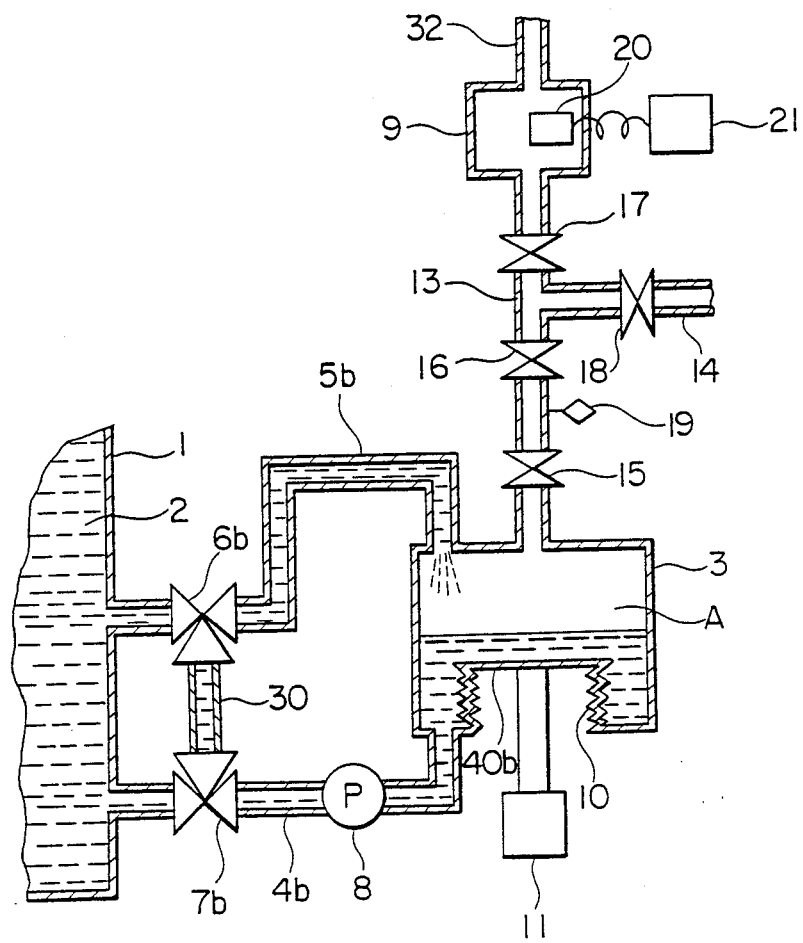

FIG. 2 shows a second embodiment of an apparatus for monitoring dissolved gas in an insulating oil according to the present invention. In FIG. 2, a three-way valve 6b attached to an oil send-out conduit 5b is communicated with a three-way valve 7b attached to an oil send-in conduit 4b through a bypass conduit 30. The three-way valves 6b and 7b are switched to change the flow of the insulating oil in the oil send-out conduit 5b, the oil send-in conduit 4b and the bypass conduit 30 which form an insulating oil circulating passage. The remaining construction is similar to that of FIG. 1.

When the monitor in FIG. 2 is operated, a plate 40b is moved upwards to a predetermined position by a driving device 11, and the send-in conduit 4b, the send-out conduit 5b, the bypass conduit 30 and a gas extracting chamber 3 are filled with the insulating oil 2 from the tank 1 through the three-way valves 6b and 7b. Then, the three-way valves 6b and 7b are set to only communicate the tank 1 with the oil send-in conduit 4b and the oil send-out conduit 5b. Thereafter, the insulating oil 2 is circulated through the conduits 4b and 5b by a pump 8 between the tank 1 and the gas extracting chamber 3 such that the insulating oil 2 in the gas extracting chamber 3 is a sample of the insulating oil 2 in the tank 1. At this time, since the insulating oil circulating passage and the gas extracting chamber 3 are filled with the insulating oil 2, the gas dissolved in the insulating oil 2 is not extracted therefrom. The operation of the pump 8 is therefore stopped and the three-way valves 6b and 7b are switched to communicate the bypass conduit 30 with the gas extracting chamber 3, thereby circulating the insulating oil 2 between the bypass conduit 30 and the gas extracting chamber 3. In this state, the plate 40b is moved downwards by the driving device 11 to extract the dissolved gas from the insulating oil within the gas extracting chamber 3. Thus, a space A under pressure reduction is formed by the dissolved gas generated in the upper portion of the gas extracting chamber 3. Next, the pump 8 is operated to inject the insulating oil 2 into the space A under pressure reduction from the gas extracting chamber 3 through the oil send-in conduit 4b, the bypass conduit 30 and the oil send-out conduit 5b. Thus, the dissolved gas is forcibly extracted from the insulating oil 2 within the gas extracting chamber 3 to balance the density of the dissolved gas in the space A with the density of the gas dissolved in the insulating oil 2 within the gas extracting chamber 3 for a short time. Thereafter, the operation of the pump 8 is stopped.

Then, as described in the first embodiment of the present invention, valves 15, 16 and 18 are opened and a valve 17 is closed to flow purified air into the space A through an air conduit 14 and a gas conduit 13, thereby forming a mixture of the dissolved gas and the air within the space A. The valve 18 is then closed and the valve 17 is opened, and the three-way valve 6b is switched to flow the insulating oil 2 from the tank 1 into the gas extracting chamber 3, thereby forcing the mixed gas in the gas extracting chamber 3 to the gas detecting chamber 9 through the gas conduit 13. The components of the dissolved gas in the mixed gas are thus measured by a gas detector having a gas detecting element 20 and a detector body 21 electrically connected thereto. Thereafter, when the level of the insulating oil 2 flowing into the gas extracting chamber 3 and the gas conduit 13 reaches the level of an oil level detector 19 disposed between the valves 15 and 16, the valves 15, 16 and 17 are closed, and the three-way valve 6b is switched to communicate the bypass conduit 30 with the oil send-out conduit 5b, thereby completing the measurement of the components of the dissolved gas.

As in the first embodiment, the mixed gas in the gas extracting chamber 3 may be transmitted to the gas detecting chamber 9 by moving the plate 40b upwards using the driving device 11 instead of transmitting the insulating oil in the tank 1 into the gas extracting chamber 3.

According to the second embodiment in which the insulating oil circulating passage comprises the bypass conduit 30 as well as the send-in and send-out conduits 4b and 5b, effects similar to those obtained in the first embodiment can be obtained.

Figure 3:
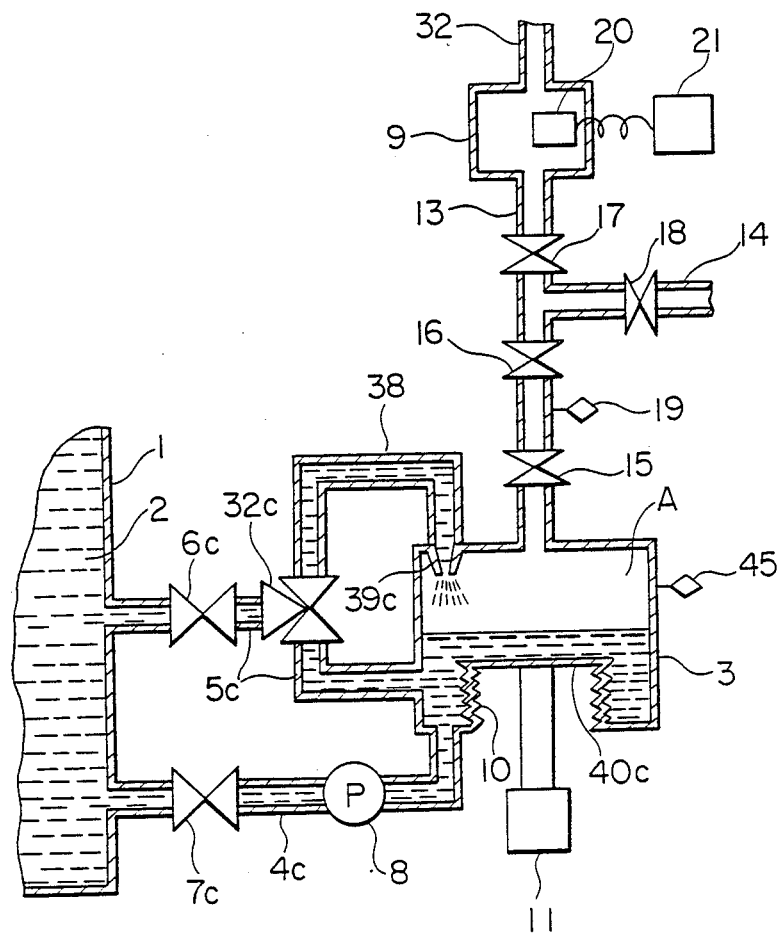

FIG. 3 shows a third embodiment of an apparatus for monitoring dissolved gas in an insulating oil according to the present invention. In FIG. 3, an insulating oil circulating passage comprises an oil send-in conduit 4c and an oil send-out conduit 5c. An oil injecting conduit 38 is connected at one end thereof through a three-way valve 32c to a portion of the oil send-out conduit 5c between a valve 6c attached thereto and a gas extracting chamber 3, and the other end 39c of the oil injecting conduit 38 is in the shape of a nozzle and connected to the upper portion of the gas extracting chamber 3. The send-out conduit 5c is connected to the lower portion of the gas extracting chamber 3. An oil level detector 45 is disposed to detect the level of the insulating oil 2 within the gas extracting chamber 3. The remaining construction is similar to that of the first embodiment shown in FIG. 1.

In this third embodiment, when a driving device 11 is driven to move a plate 40c upwards to an upper limit of location thereof, the oil send-in conduit 4c, the oil send-out conduit 5c, the oil injecting conduit 38 and the gas extracting chamber 3 are filled with the insulating oil 2 from the tank 1 through the valves 6c, 7c and 32c. Then, the three-way valve 32c is switched such that the insulating oil 2 flowing through the valve 6c is not transmitted to the oil injecting conduit 38. With the valves 6c and 7c still open, a pump 8 is operated to circulate the insulating oil 2 through the conduits 4c and 5c between the tank 1 and the gas extracting chamber 3. During the circulation of the insulating oil 2, the gas dissolved in the insulating oil is not extracted therefrom since the oil send-in conduit 4c, the oil send-out conduit 5c, the oil injecting conduit 38 and the gas extracting chamber 3 are filled with the insulating oil. Thus, the insulating oil 2 in the tank 1 is completely mixed up by the circulation thereof so that the insulating oil 2 within the gas extracting chamber 3 becomes a sample typical of the insulating oil 2 in the tank 1. Thereafter, the operation of the pump 8 is stopped and the valves 6c and 7c are closed.

In the above state, the plate 40c is moved downwards by the driving device 11 to extract a dissolved gas from the insulating oil 2 within the gas extracting chamber 3. Thus, a space A of the dissolved gas under pressure reduction is formed in the upper portion of the extracting chamber 3. The three-way valve 32c is then switched and the valve 6c is opened to communicate the oil injecting conduit 38 with the tank 1 through a portion of the oil send-out conduit 5c having the valve 6c, so that the insulating oil 2 is injected into the space A under pressure reduction through the nozzle-shaped end 39c of the oil injecting conduit 38. At this time, the insulating oil 2 is dispersed and the dissolved gas is forcibly extracted from the insulating oil 2 within the space A under pressure reduction. Then, when the level of the insulating oil 2 in the gas extracting chamber 3 reaches the level of the oil level detector 45, the three-way valve 32c is switched and the valve 6c is closed so as not to transmit the insulating oil 2 in the gas extracting chamber 3 to the oil injecting conduit 38.

As described in the first embodiment shown in FIG. 1, the dissolved gas in the as extracting chamber 3 is mixed up with purified air from a gas conduit 13 and an air conduit 14 through valve 18 attached thereto and valves 15 and 16. Then, the valve 18 is closed and valve 17 is opened and the three-way valve 32c is switched to flow the insulating oil 2 from the tank 1 into the gas extracting chamber 3 through the send-out conduit 5c, thereby forcing the mixture within the gas extracting chamber 3 to the gas detecting chamber 9 through a gas conduit 13. Thereafter, the components of the dissolved gas in the gas detecting chamber 9 are measured by a gas detector having a gas detecting element 20 and a detector body 21 electrically connected thereto. When the level of the insulating oil 2 flowing through the gas conduit 13 reaches the level of oil level detector 19 between the valves 15 and 16, the valves 6c, 17, 16 and 15 are closed, thereby completing the measurement of the components of the dissolved gas.

In the third embodiment mentioned above, the effects similar to those obtained in the first embodiment of FIG. 1 can be obtained.

Figure 4:
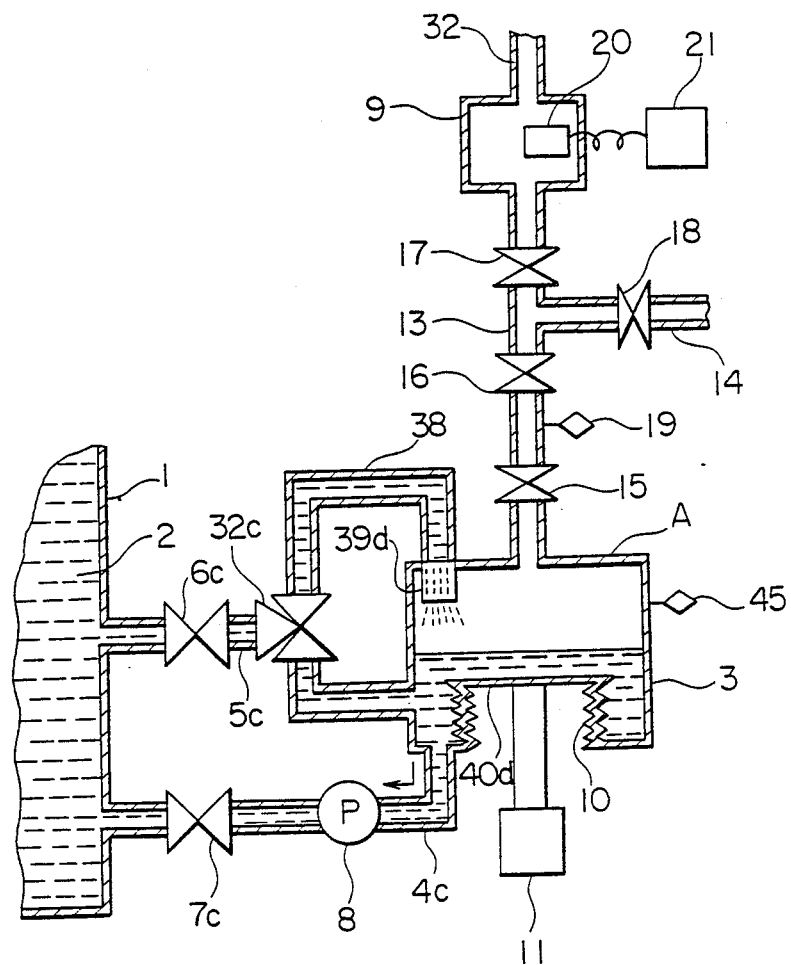

FIG. 4 shows a fourth embodiment of an apparatus for monitoring dissolved gas in an insulating oil according to the present invention which is similar to the third embodiment except that a filter 39d instead of a nozzle is disposed at the end tip of oil injecting conduit 38. The filter 39d is disposed to filter foreign matter in the insulating oil flowing from the tank 1 through a portion of oil send-out conduit 5c having valve 6c and the oil injecting conduit 38 into gas extracting chamber 3. The insulating oil in the oil injecting conduit 38 is preferably injected and dispersed to space A under pressure reduction in the gas extracting chamber 3 through the filter 39d, thereby forcibly extracting dissolved gas from the insulating oil 2.

In the fourth embodiment mentioned above, in addition to the effects similar to those obtained in the first embodiment of FIG. 1, there is also the effect wherein foreign matter in the insulating oil is filtered out by the filter 39d.

Figure 5:
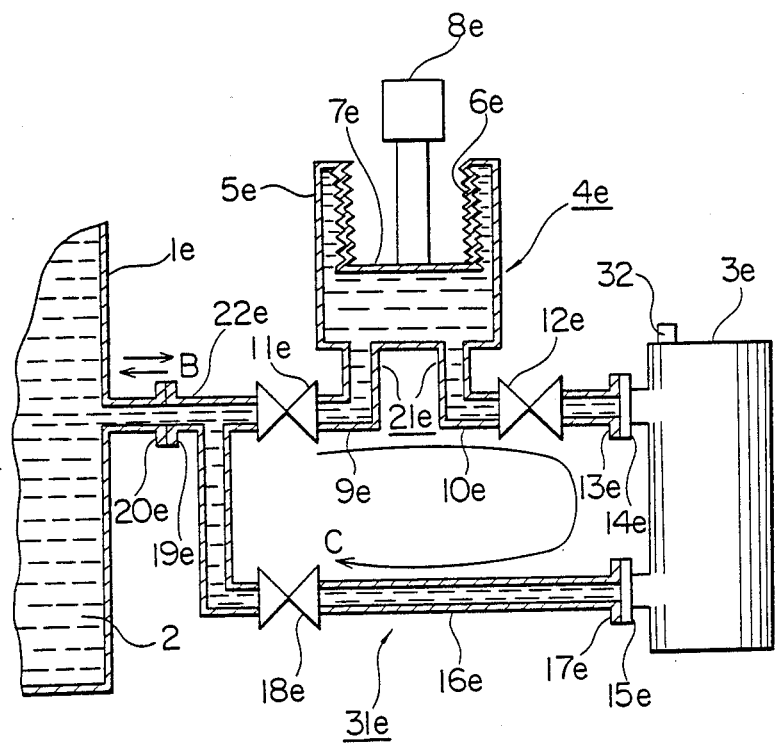

FIG. 5 shows a fifth embodiment of an apparatus for monitoring dissolved gas in an insulating oil according to the present invention. In FIG. 5, an unillustrated electrical apparatus is disposed within a tank 1e and is immersed in insulating oil 2 therein. The tank 1e is provided with a single connecting oil port 20e. The single connecting oil port 20e is connectable to a connecting port 19e of a first oil conduit device 21e having flow-in and flow-out conduits 9e and 10e, respectively. Valves 11e and 12e are respectively attached to the flow-in and flow-out conduits 9e and 10e and are opened or closed to pass or interrupt the flow of the insulating oil therethrough. A oil sampling device 4e is connected between the flow-in and flow-out conduits 9e and 10e. The sampling device 4e comprises a cylindrical sampling chamber 5e the bottom of which isconnected to one end of both the flow-in and flow-out conduits 9e and 10e, a bellows 6e connected at its one end to the inner circumferential edge of the sampling chamber 5e, a plate 7e connected to the other end of the bellows 6e, and a driving device 8e attached to the plate 7e to reciprocate the plate 7e.

A connecting port 13 at the other end of the flow-out conduit 10e is connected to a connecting port 14e of a dissolved gas monitoring apparatus 3e for detecting gas generated by abnormal phenomena such as arc discharge, corona discharge or local heating within the electrical apparatus in the tank 1e at the early stage of the phenomena. The dissolved gas monitoring apparatus 3e comprises a means for extracting the dissolved gas from the insulating oil as in the first embodiment, and a means for measuring the components of the dissolved gas form the extracting means and connected to the exterior of the monitor as in the first embodiment. Therefore, the dissolved gas monitoring device 3e corresponds to the device shown within the dotted lines in FIG. 1. The insulating oil 2 in the tank 1e is transmitted to the dissolved gas monitoring apparatus 3e by the sampling device 4e through the flow-in and flow-out conduits 9e and 10e.

Another connecting port 15e of the dissolved gas monitoring device 3e is connected to a connecting port 17e of a second oil conduit device 31e. The second oil conduit device 31e comprises an oil send-out conduit 16e having the connecting port 17e and connected to a portion of the oil flow-in conduit 9e between the connecting port 19e and the valve 11e, and a valve 18e attached to the oil send-out conduit 16e and opened or closed to pass or interrupt the flow of the insulating oil therethrough.

The first and second oil conduit devices 21e and 31e constitute an insulating oil circulating passage for circulating the insulating oil 2 from the tank 1e as shown by an arrow C of FIG. 5. A portion 22e of the oil flow-in conduit 9e on the tank side thereof forms a passage for transmitting the insulating oil 2 from the tank 1 into the oil sampling device 4e and for returning the insulating oil through the oil send-out conduit 16e to the tank 1, as shown by arrows B of FIG. 5.

In the construction mentioned above, when the monitor is operated, the valve 11e is opened and the plate 7e is located in the lowermost position thereof in FIG. 5. Then, the plate 7e is moved upwards by the driving device 8e to fill the oil flow-in conduit 9e and the sampling chamber 5e with the insulating oil 2 from the tank 1e. Thereafter, the valve 11e is closed and the valves 12e and 18e are opened, and the plate 7e is moved downwards by the driving device 8e to transmit the insulating oil within the sampling chamber 5e through the oil flow-out conduit 10e to the dissolved gas monitoring device 3e. In the dissolved gas monitoring device 3e, dissolved gas is extracted from the insulating oil transmitted from the oil flow-out conduit 10e by the extracting means and the components thereof are measured by the gas detecting means as in the first embodiment. The insulating oil in the gas monitoring device 3e is returned to the tank 1e through the oil send-out conduit 16e and the passage 22e.

In the fifth embodiment mentioned above, the oil sampling device 4e constitutes a means for circulating the insulating oil and is disposed between the oil flow-in and flow-out conduits 9e and 10e. However, similar effects can be obtained even when another insulating oil circulating means such as a positive displacement pump is disposed instead of the oil sampling device 4e in the insulating oil circulating passage to circulate the insulating oil. Further, although the dissolved gas monitoring apparatus 3e is disposed downstream of the oil sampling device 4e, similar effects can be obtained even if the monitoring device 3e is disposed upstream of the oil sampling device 4e.

In accordance with the fifth embodiment of the present invention, an ordinary single drain port provided in any conventional tank of an electrical apparatus can be used as a connecting port for sampling insulating oil from the tank for gas monitoring.

What is claimed is:

1. A monitor for gas dissolved in an electrically insulating oil in which an electrical apparatus is immersed in a tank, said monitor comprising:
   sampling means connected to the tank for sampling a portion of the insulating oil from the electrical apparatus;
   extracting means connected to said sampling means for extracting a volume of dissolved gas from said portion of the insulating oil in said sampling means;
   measuring means for measuring components of the dissolved gas;
   means for delivering substantially all of the volume of dissolved gas to said measuring means;
   means for exhausting from the monitor all of the volume of dissolved gas delivered to said measuring means; and
   means for returning said portion of the insulating oil in said extracting means to the electrical apparatus.

2. A monitor for gas dissolved in an electrically insulating oil in which an electrical apparatus is immersed in a tank, and monitor comprising:
   circulating means connected to the tank for circulating the insulating oil from the tank;
   control means disposed in the circulating means for passing or interrupting the flow of insulating oil through the circulating means;
   extracting means disposed in the circulating means for extracting a volume of dissolved gas from the insulating oil within the extracting means in cooperation with the control means;

gas detecting means in communication with the extracting means for measuring components of the dissolved gas;

means for delivering substantially all of the volume of dissolved gas from said extracting means to said detecting means; and exhausting means for exhausting from the monitor substantially all of the volume of dissolved gas.

3. A monitor for gas dissolved in an electrically insulating oil as claimed in claim 2 wherein said extracting means comprises a gas extracting chamber disposed in the circulating means for sampling a portion of the insulating oil, said circulating means comprises a conduit connected at both ends thereof to the tank, said conduit being connected to the gas extracting chamber, said gas detecting means comprises a gas detecting chamber connected to the gas extracting chamber, and a gas detector connected to said gas detecting chamber, and said means for delivering substantially all of the volume of dissolved gas includes an insulating oil detector in the connection between said gas detecting chamber and the gas extracting chamber to detect when substantially all the volume of dissolved gas had been delivered from said extracting means.

4. A monitor for gas dissolved in an electrically insulating oil as claimed in claim 3 wherein said extracting means further comprises a plate disposed in the gas extracting chamber, a bellows attached to the plate and the gas extracting chamber, and a driving device for moving the plate in one direction to extract the dissolved gas from the insulating oil within the gas extracting chamber and in an opposite direction to deliver the dissolved gas to said gas detecting chamber from the gas extracting chamber.

5. A monitor for gas dissolved in an electrically insulating oil as claimed in claim 4 wherein said extracting means further comprises a vibrator for vibrating the insulating oil within the gas extracting chamber.

6. A monitor for gas dissolved in an electrically insulating oil as claimed in claim 2 wherein said control means comprises valves attached to the conduit.

7. A monitor for gas dissolved in an electrically insulating oil as claimed in claim 2 wherein said extracting means comprises a gas extracting chamber disposed in the circulating means for sampling a portion of the insulating oil, said circulating means comprises a send-out conduit for transmitting the insulating oil in the tank to the gas extracting chamber, a send-in conduit for transmitting the insulating oil in the gas extracting chamber to the tank and a bypass conduit connected to the send-in and send-out conduits therebetween to form a portion of a circulating path of the insulating oil from the gas extracting chamber, said control means controlling the flow of the insulating oil so that the circulating oil circulates through the send-out conduit, the gas extracting chamber, the send-in conduit and the bypass conduit.

8. A monitor for gas dissolved in an electrically insulating oil as claimed in claim 7 wherein said control means comprises three-way valves for connecting the bypass conduit to the send-in and send-out conduits.

9. A monitor for gas dissolved in an electrically insulating oil as claimed in claim 7 wherein said extracting means comprises a plate disposed in the gas extracting chamber, a bellows attached to the plate and the gas extracting chamber, and a driving device for moving the plate in one direction to extract the dissolved gas from the insulating oil within the gas extracting chamber and in an opposite direction to deliver the dissolved gas to said gas detecting chamber from the gas extracting chamber.

10. A monitor for gas dissolved in an electrically insulating oil as claimed in claim 2 wherein said extracting means comprises a gas extracting chamber disposed in the circulating means for sampling a portion of the insulating oil, and oil injecting conduit connected at one end thereof to the circulating means, the other end of the oil injecting conduit being in the shape of a nozzle and connected to the upper portion of the gas extracting chamber, said control means controlling the flow of the insulating oil in the circulating means and the oil injecting conduit such that the insulating oil in the oil injecting conduit is injected into the gas extracting chamber.

11. A monitor for gas dissolved in an eletrically insulating oil as claimed in claim 10 wherein said control means comprises a three-way valve for connecting the oil injecting conduit to the circulating means.

12. A monitor for gas dissolved in an electrically insulating oil as claimed in claim 10 wherein said extracting means further comprises a plate disposed in the gas extracting chamber, a bellows attached to the plate and the gas extracting chamber, and a driving device for moving the plate in one direction to extract the dissolved gas from the insulating oil within the gas extracting chamber and in an opposite direction to deliver the dissolved gas to said gas detecting chamber from the gas extracting chamber.

13. A monitor for gas dissolved in an electrically insulating oil as claimed in claim 2 wherein said extracting means comprises a gas extracting chamber disposed in the circulating means for sampling said portion of the insulating oil, an oil injecting conduit connected at one end thereof to the circulating means, the other end of the oil injecting conduit being connected to the upper portion of the gas extracting chamber and provided with a filter for filtering the insulating oil from the oil injecting conduit, said control means controlling the flow of the insulating oil in the circulating means and the oil injecting conduit such that the insulating oil in the oil injecting conduit is injected into the gas extracting chamber.

14. A monitor for gas dissolved in an electrically insulating oil as claimed in claim 13 wherein said control means comprises a three-way valve for connecting the oil injecting conduit to the circulating means.

15. A monitor for gas dissolved in an electrically insulating oil as claimed in claim 13 wherein said extracting means further comprises a plate disposed in the gas extracting chamber, a bellows attached to the plate and the gas extracting chamber, and a driving device for moving the plate in one direction to extract the dissolved gas from the insulating oil within the gas extracting chamber and in an opposite direction to deliver the dissolved gas to said gas detecting chamber from the gas extracting chamber.

16. A monitor for gas dissolved in an electrically insulating oil in which an electrical apparatus is immersed in a tank, said monitor comprising:

circulating means connected to a single port disposed in the tank and having first and second conduit devices connected to the single port of the tank to circulate the insulating oil of the tank;

control means attached to the circulating means for passing or interrupting the flow of the insulating oil through the circulating means;

a dissolved gas monitoring device connected to the first and second conduit devices of the circulating means, said device comprising:

means for extracting a volume of dissolved gas from the insulating oil in cooperation with the control means;

means for measuring the components of the dissolved gas;

means for delivering substantially all of the volume of dissolved gas to said measuring means; and means for discharging all of the measured volume of dissolved gas to the exterior of the monitor.

17. A monitor for gas dissolved in an electrically insulating oil as claimed in claim 16 wherein said circulating means comprises an oil sampling device disposed in the first conduit device and having a sampling chamber for storing a portion of the insulating oil sampled from the tank, a pressure plate disposed in the sampling chamber, a bellows connected to the pressure plate and the sampling chamber, and a driving device for reciprocating the pressure plate to extract the dissolved gas in one direction of motion of the driving device and transmit the dissolved gas and the insulating oil in the sampling chamber into the dissolved gas monitoring device in an opposite direction of motion of the driving device.

18. A monitor for gas dissolved in an electrically insulating oil as claimed in claim 16 wherein said control means comprises valves attached to the first and second conduit devices of the circulating means.

* * * * *

UNITED STATES PATENT AND TRADEMARK OFFICE
CERTIFICATE OF CORRECTION

PATENT NO. : 4,763,514

DATED : August 16, 1988

INVENTOR(S) : Naito et al

It is certified that error appears in the above-identified patent and that said Letters Patent is hereby corrected as shown below:

Column 7, line 24, "isconnected" has been changed to --is connected--;

Column 7, line 31, "13" has been changed to --13e--.

Signed and Sealed this

Twenty-eighth Day of February, 1989

Attest:

DONALD J. QUIGG

Attesting Officer

Commissioner of Patents and Trademarks